United States Patent [19]
Buchert et al.

[11] Patent Number: 5,854,047
[45] Date of Patent: *Dec. 29, 1998

[54] MANNANASE ENZYMES, GENES CODING FOR THEM AND A METHOD FOR ISOLATING THE GENES, AS WELL AS A PROCESS FOR BLEACHING OF LIGNOCELLULOSIC PULP

[75] Inventors: Johanna Buchert, Espoo; Matti Siika-aho, Helsinki; Liisa Viikari, Helsinki; Merja Penttilä, Helsinki; Anu Saloheimo, Helsinki; Marjatta Ranua, Lohja, all of Finland

[73] Assignee: Röhm Enzyme Finland OY, Rajamäki, Finland

[ * ] Notice: The term of this patent shall not extend beyond the expiration date of Pat. No. 5,661,021.

[21] Appl. No.: 911,020

[22] Filed: Aug. 13, 1997

Related U.S. Application Data

[63] Continuation of Ser. No. 341,568, filed as PCT/FI93/00219 May 24, 1993, Pat. No. 5,661,021.

[30] Foreign Application Priority Data

| | | | |
|---|---|---|---|
| May 22, 1992 | [FI] | Finland | 922373 |
| Mar. 17, 1993 | [FI] | Finland | 931193 |

[51] Int. Cl.$^6$ .............................. C12N 9/42; C12N 1/20; C12N 1/14; C12N 1/16
[52] U.S. Cl. ................. 435/209; 435/252.3; 435/254.11; 435/254.6; 435/256.7; 435/256.8
[58] Field of Search .............................. 435/209, 252.3, 435/254.11, 254.6, 256.7, 256.8

[56] References Cited

U.S. PATENT DOCUMENTS

| | | | |
|---|---|---|---|
| 4,725,544 | 2/1988 | Tan et al. | 435/200 |
| 5,661,021 | 8/1997 | Buchert et al. | 435/209 |

FOREIGN PATENT DOCUMENTS

WO9118974  12/1991  WIPO .

OTHER PUBLICATIONS

Bisaria et al. (1981) Enzyme Microb. Technol. 3:90–104.
Torrie et al. (1991) Biodeterior. Biodegr. 8:542–544.
Torrie et al. (1990) Appl. Microb. Technol. 34: 303–307.
Mondou et al. (1986) Gene 49: 323–329.
Vlasenko et al. (1990) Appl. Biochem. Microbiol. 25(5): 511–519.
Nevalainen et al. (1978) Appl. Environ. Microbiol. 35(1): 11–16.
Zurbriggen et al. (1990) J. Biotechnol. 13:267–278.
Penttila et al. (1987) Yeast 3: 175–185.
Protein purification methods, a practical approach, E.L.V. Harris and S. Angal, eds., IRL Press at Oxford University Press, NY, NY 1989.
Torrie et al., Dialog Information Services, File 357, Biotechnology Abstracts, Dialog Accession No. 146065, DBA Accession No. 93–04177 (1991).
Torrie et al., Dialog Info. Services, File 5, Biosis, Dialog Accession No. 8150876, Biosis No. 91071876 (1990).
Clark et al., Abstract 4th Int. Conf. on Biotechnology in the Pulp and Paper Industry, Raleigh 1989, pp. 39–40.
Clark et al., Proc. 45th APPITA Annual General Conference, Melbourne, vol. I, pp. 193–200 (1991).
Kantelinen et al., (1988) International Pulp Bleaching Conference, Tappi Proceedings, 1–9.
Poutanen et al., Journal of Biotechnology, vol. 6, pp. 49–60 (1987).
Reese et al., Canadian Journal of Microbiology, vol. 11, pp. 167–183 (1965).
Simonson, Svensk Papperstidning 74, pp. 691–700 (1971).
Viikari et al., Enzymes in Biomass Conversion, ACS Symp. Ser. 460, American Chemical Society, Washington, D.C., pp. 12–22 (1991).
Clark et al., Biotechnology in Pulp and Paper Manufacture, Chapter 14, pp. 153–167 (1990).
Zurbriggen et al. (1991) J. Biotechnol. 17: 133–146.
Simmons, E. (1977) Classification of Some Cellulase–Producing *Trichoderma* Species. Abstracts of the Second International Mycological Congress, Tampa FL, p. 618.

*Primary Examiner*—Robert A. Wax
*Assistant Examiner*—Lisa J. Hobbs
*Attorney, Agent, or Firm*—Birch, Stewart, Kolasch & Birch, LLP

[57] ABSTRACT

The present invention relates to a DNA sequence, which codes for endomannanase produced by fungi of the genus Trichoderma and transferred into a yeast or fungus strain induces that strain to produce endomannanase, as well as to a method for isolating genes coding for endomannanases. The invention also relates to vectors, yeast strains and fungal strains containing the DNA sequence. Furthermore, the invention provides an enzyme product containing at least one endomannanase, which contains at least one of the following endomannanases produced by fungi of the Trichoderma genus: an enzyme having mannanase activity and an isoelectric point (pI) of about 3.8, an enzyme having mannanase activity and a pI of about 4.1, an enzyme having mannanase activity and a pI of about 4.5, an enzyme having mannanase activity and a pI of about 5.4 and an enzyme having mannanase activity and a pI of about 6.5, the isoelectric points being determined by isoelectric focusing. The endomannanase enzyme and enzyme products according to the invention can be used for hydrolyzation of mannopolymers, in particular in connection with bleaching of lignocellulosic pulps.

9 Claims, 3 Drawing Sheets

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 536 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Trichoderma reesei
        ( B ) STRAIN: QM9414

( x i ) SEQUENCE DESCRIPTION: SEQ ID NO: 1:

```
GAATTCGGCA  CGAGAGTCTC  TCCTTTTTTT  CTCACTATAT  CTTTCCTTTG  TCCATGTTGC      60
TGTTGTCGTC  GTTGTTCTTG  AGACTATGCT  GGCCTGGTTG  GTCCGGATGA  ACTGGTGGTT     120
GGGATGGCTG  GAGCCTGTGG  AAGCGGGCTC  GCCGTGGCGT  TGGTCAACCG  ATTGTATATC     180
AGTCTATGCC  TCTGTACACT  TCGTCTCTAG  CGAAGAGGAG  TTGAATACAA  ATCTGTAAAA     240
CACTTGACTG  TGTCTTCTAG  CTATGAGACT  CCCTTGCCTA  CTGGAGCCTT  CAAGATACTT     300
TGGTACTGTA  TGAGACCACG  CCTACCTCGA  CTTCATGTTT  GAAACCAGTC  AGTAATTCTC     360
TATGAACATG  AAACAACACA  TTGATCTCTG  TAACATCTCA  TTGCATAGTA  AACCTTCTTA     420
CATTGATTAC  TGGCTATGAA  CAAAGGTTGT  AGGGTAGGTA  ACGAAAAAAA  AAAAAAAAA      480
AAAAAAAAAA  AAAAAAAAAA  AAAAAAAAAA  AAAAAAAAAA  AAAAAAAAAA  CTCGAG         536
```

( 2 ) INFORMATION FOR SEQ ID NO: 2:

( i ) SEQUENCE CHARACTERISTICS:
        ( A ) LENGTH: 243 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: Trichoderma reesei
        ( B ) STRAIN: QM9414

( x i ) SEQUENCE DESCRIPTION: SEQ ID NO: 2:

```
GAATTCGGCA  CGAGCTCTTA  ACCAACCACC  AAACTACAGC  CACCCACCAT  GTCCGCCAA      60
```

| | | | | | |
|---|---|---|---|---|---|
| GACTACTACG | TCCAGCGCCT | CCGGAGGCAG | CAGCAACGGT | TATCCTCCTC | AGCAGTACCA | 120
| CCAGCAGCAG | CAACAGCCAT | ACGGCCAGCA | GCAGCCAGGG | TATGACCAGC | AGTACCCGG | 180
| CGCCGGAGTC | GATGGAGGCC | CCGACGGAGA | GCGCGGCCTC | GGCGCGACCC | TCGTCGGCGG | 240
| CGG | | | | | | 243

(2) INFORMATION FOR SEQ ID NO: 3:

(i) SEQUENCE CHARACTERISTICS:
        (A) LENGTH: 289 base pairs
        (B) TYPE: nucleic acid
        (C) STRANDEDNESS: single
        (D) TOPOLOGY: linear     (ii) MOLECULE TYPE: cDNA     (vi) ORIGINAL SOURCE:
        (A) ORGANISM: Trichoderma reesei
        (B) STRAIN: QM9414

(xi) SEQUENCE DESCRIPTION: SEQ ID NO: 3:

| | | | | | |
|---|---|---|---|---|---|
| CTGCAGCCGC | CGGAGCCATT | GGGGCGAATC | TCATTGAGAA | CGCATACAAG | AAGCACAAGG | 60
| AGGAAAAGAT | GTACAATGAT | GGCGGACACC | ATGGCCATCA | CCACCATTCG | CATCATCATA | 120
| AGCACTAGAA | TGATTTGATG | AAGAATATGA | CATTGCATGC | CTGCTACATA | CGTAGATTAT | 180
| GATTGGGGGA | GGGGCGTTTT | TGATGAATAT | ATATATATAT | CAATAAAAAA | AAAAAAAAAA | 240
| AAAAAAAAAA | AAAAAAAAAA | AAAAAAAAAA | AAAAAAAAAA | AAACTCGAG | | 289

(2) INFORMATION FOR SEQ ID NO: 4:

(i) SEQUENCE CHARACTERISTICS:
        (A) LENGTH: 865 base pairs
        (B) TYPE: nucleic acid
        (C) STRANDEDNESS: single
        (D) TOPOLOGY: linear     (ii) MOLECULE TYPE: cDNA     (vi) ORIGINAL SOURCE:
        (A) ORGANISM: Trichoderma reesei
        (B) STRAIN: QM9414

(xi) SEQUENCE DESCRIPTION: SEQ ID NO: 4:

| | | | | | |
|---|---|---|---|---|---|
| GAATTCGGCA | CGAGTTTTTT | TTTTTTTTTT | TACAGTATAC | GTTAGGTGTA | TTCGAACGAA | 60
| AGCCTGAAAT | AGGTACAAAT | AGCCACAACA | GAAACGATTG | TCTGACCTCC | ACTGAGAAAA | 120
| TCCCCCTCGT | CCCCCAGACA | GGTCTGATCA | AACACCAGCT | ATCTACCTGC | AAATGCCCCA | 180
| TATGTAGGTC | ACACAGTAAG | GAGTGGATTC | GCTATATACA | TCGGGTACGT | TCGCATCACC | 240
| CCATGGCAAG | GGAGGTGACT | TAAGCAAAAC | CGCCACTAAC | CACAAAGCTC | AACTGCATAG | 300
| TATCGACTTC | AAGGAAAACA | CGGACAAATA | ATCATCATGG | TTGCCTTTTG | CAGCCTCATC | 360
| TGCGCTCTCA | CGAGGCATCG | CCAGTACTCT | GGCGATGCCC | ACAGGCTCGA | GCCTGAGAGC | 420
| AGTGTCAACG | TCACAGAGCG | TGGCATGTAC | GACTTTGTTC | TTGGAGCTCA | CAATGATCAT | 480
| CGCCGTCGTG | CTAGCATCAA | CTACGACCAA | AACTACCAAA | CTGGCGGACA | AGTCAGCTAT | 540
| TCGCCTTCCA | ACACTGGCTT | CTCAGTGAAC | TGGAACACTC | AAGATGACTT | TGTTGTGGGC | 600
| GTTGGTTGGA | CGACTGGATC | TTCTGCTCCC | ATCAACTTTG | GCGGCTCTTT | TAGTGTCAAC | 660
| AGCGGAACTG | GCCTGCTTTC | CGTCTATGGC | TGGAGCACCA | ACCCACTGGT | TGAGTACTAC | 720
| ATCATGGAGG | ACAACCACAA | CTACCCAGCA | CAGGGCACCG | TCAAGGAAC | CGTCAACAGC | 780
| GACGGGGCAC | TTACACCATC | TTGGGGGATT | ACCGTGTAAC | GAGCCTTCCA | TCCAGGGTAC | 840

```
AGCGCCTTCA  ACCGTACATT  TCCGT                                                                      865
```

(2) INFORMATION FOR SEQ ID NO: 5:

(i) SEQUENCE CHARACTERISTICS:
        (A) LENGTH: 319 base pairs
        (B) TYPE: nucleic acid
        (C) STRANDEDNESS: single
        (D) TOPOLOGY: linear     (ii) MOLECULE TYPE: cDNA     (vi) ORIGINAL SOURCE:
        (A) ORGANISM: Trichoderma reesei
        (B) STRAIN: QM9414

(xi) SEQUENCE DESCRIPTION: SEQ ID NO: 5:

```
CAGATGAACT  ACCCAGGTTG  TCGCTGTCGA  AAGGCTGGGG  TGGTAGTGGT  TCTGCCTCAC   60
AGAGTGTCAG  CAACTAGGTT  CTGTTGATGT  TGACTTGGAG  TGGATGAGGG  GTTTGAGCTG  120
GTATGTAGTA  TTGGGGTGGT  TAGTGAGTTA  ACTTGACAGA  CTGCACTTTG  GCAACAGAGC  180
CGACGATTAA  GAGATTGCTG  TCATGTAACT  AAAGTAGCCT  GCCTTTGACG  CTGTATGCTC  240
ATGATACATG  CGTGACATCG  AAATATATCA  GCCAAAGTAT  CCGTCCGGCG  AAAAAAAAAA  300
AAAAAAAAAA  AAACTCGAG                                                  319
```

(2) INFORMATION FOR SEQ ID NO: 6:

(i) SEQUENCE CHARACTERISTICS:
        (A) LENGTH: 15 amino acids
        (B) TYPE: amino acid
        (C) STRANDEDNESS: single
        (D) TOPOLOGY: linear     (ii) MOLECULE TYPE: protein     (iv) FRAGMENT TYPE: N-terminal     (xi) SEQUENCE DESCRIPTION: SEQ ID NO: 6:

```
Xaa  Xaa  Xaa  Phe  Val  Thr  Ile  Ser  Xaa  Thr  Gln  Xaa  Xaa  Ile  Asp
1              5                        10                       15
```

(2) INFORMATION FOR SEQ ID NO: 7:

(i) SEQUENCE CHARACTERISTICS:
        (A) LENGTH: 15 amino acids
        (B) TYPE: amino acid
        (C) STRANDEDNESS: single
        (D) TOPOLOGY: linear     (ii) MOLECULE TYPE: protein     (iv) FRAGMENT TYPE: N-terminal     (xi) SEQUENCE DESCRIPTION: SEQ ID NO: 7:

```
Xaa  Xaa  Xaa  Xaa  Xaa  Thr  Ile  Ser  Gly  Thr  Gln  Xaa  Xaa  Ile  Asp
1              5                        10                       15
```

MANNANASE ENZYMES, GENES CODING FOR THEM AND A METHOD FOR ISOLATING THE GENES, AS WELL AS A PROCESS FOR BLEACHING OF LIGNOCELLULOSIC PULP

This application is a continuation of application Ser. No. 08/341,568 filed on Nov. 22, 1994, now U.S. Pat. No. 5,661,021, the entire contents of which are hereby incorporated by reference, which was the national phase filing from PCT International Application No. PCT/FI93/00219 filed on May 24, 1993.

The present invention relates to a DNA sequence which codes for mannanase enzymes. The invention also concerns vectors, yeast and fungus strains containing said DNA sequence. Furthermore the invention relates to a method for isolating genes coding for mannanases and to a method for constructing yeast strains capable of expressing mannanase. The invention also provides an enzyme product containing at least one mannanase and a method for preparing mannanase enzymes and enzyme products. Finally, the invention concerns a process for hydrolyzing mannopolymers and to a process for bleaching lignocellulosic pulps.

The main components of wood are cellulose, lignin and hemicellulose. Softwood mainly comprises arabino-4-O-methylglucuronoxylan, whereas hardwood xylan consists of O-acetyl-4-O-methylglucuronoxylan. The glucomannan polymers are formed by a main chain consisting of glucose and mannanose units. The main chain is substituted with galactose and acetylunits. There are only small amounts (2–5%) of glucomannanes in hardwood and the glucomannan of hardwood trees differs structurally from that of softwood trees in the sense that it is not acetylated nor does it contain galactose side groups (Timell 1967). During chemical pulping the relative amounts of hemicelluloses is changed compared to that of the native tree. The main hemicellulose component of both softwood and hardwood kraft pulp is xylan (Sjöström 1977). Softwood pulp contains also large amounts of glucomannan. During pulping, a part of the hemicellulose of the wood is dissolved because of the very alkaline cooking liquor. When the cooking is continued, pH decreases and xylan with no or few side chains will start to precipitate on the surface of the cellulose fibers (Yllner and Enström 1956, Yllner et al. 1957). This xylan reprecipitation takes place simultaneously with the precipitation of dissolved lignin. The glucomannan behaves in alkaline cooking conditions in a different way compared to xylan. Softwood glucomannanes are subjected to a partial decomposition already at approx. 130° C. and, thus, the relative proportion of glucomannan in pulp is smaller than in the original softwood (Sjöström 1977). The glucomannan remaining in the fiber is, however, very stable (Simonson 1971). Glukomannan is believed to be evenly distributed within the fiber, wheras the xylan concentration is largest on the surface of the fiber (Luce 1964).

After chemical pulping, the pulp will contain darkened residual lignin which is removed by bleaching. In conventional chlorine bleaching the ligning is dissolved using chlorine or chlorine dioxide. Nowadays oxygen bleaching, hydrogen peroxide and combinations of these and the former are also often used.

It has been found out that the bleachability of the fibres can be improved by using hemicellulases, in particular xylanase, (Kantelinen et al 1988, Viikari et al 1991a). The amounts of enzymes needed for achieving bleaching are small and an enzymatic treatment can easily be combined with pulping processes. In the present applications, thus far enhanced bleachability of the fibres has been achieved by hydrolyzing the fibre xylan. According to the present belief, the xylanases act mainly on the xylan located on the surface of the pulp fibres (Kantelinen et al 1991). Hemicellulase (xylanase) treatments have been combined with various bleaching sequences. The use of enzymes in bleaching has been evaluated by peroxide delignification (Viikari et al. 1986, Viikari et al. 1987, Viikari et al. 1990) and by various chlorine bleaching sequences carried out on laboratory scale. Industrially enzyme treatments have been combined with different chlorine bleaching sequences and also with various multistage peroxide bleaching sequences (Viikari et al. 1991b). However, even if the peroxide bleaching is carried out as a multistage bleaching sequence, the brightness of pulp bleached entirely without chlorine chemicals remains lower than that of chlorine bleached pulp.

The use of bacterial and fungal mannanases for pretreatment of pulp before bleaching has been studied (Clark et al 1990, Clark et al 1991). The mannanase preparations used have been produced by the organisms *Bacillus subtilis, T. harzianum* and *Aspergillus niger*. The products are reported slightly to improve bleaching but, because of the impurities which the products contain, the influence of the mannanase component has not been shown.

It is an aim of the present invention to eliminate the problems associated with the prior art and to provide a completely novel enzyme product which can be used, for instance, in bleaching of cellulose pulp.

The present invention is based on the surprising finding that the mannanase enzymes produced by fungi of the genus Trichoderma are particularly well suited for hydrolyzing mannopolymers and, thus, for treatment of cellulose pulp, for instance.

It is known in the art that the mannanase production of several fungi can be induced by using cellulose (Lyr 1963) and mannan-containing components (Reese and Shibata 1964) in the growth medium. It is also known that the fungus *Trichoderma reesei* is an efficient producer of enzymes which hydrolyze cellulose (for instance Bisaria and Ghose 1981) and xylan (Poutanen et al. 1987). *Trichoderma reesei* growing in nature can utilize not only the cellulose of plant material but also the hemicellulose part.

In the research work forming the basis of the invention it could be shown that a certain strain of *Trichoderma reesei* (Rut C-30, VTT D-86271) produces a lot of mannanase activity when cultivated in a fermentor on a culture medium containing cellulose as a carbon source and corn steep syrup as a nitrogen source. In connection with the invention, an enzyme mixture was obtained from the *Trichoderma reesei* strain which contained at least one selected from the group comprising an enzyme having mannanase activity and an isoelectric point (pI) of about 3.8, an enzyme having mannanase activity and a pI of about 4.1, an enzyme having mannanase activity and a pI of about 4.5, an enzyme having mannanase activity and a pI of about 5.4 and an enzyme having mannanase activity and a pI of about 6.5. The isoelectric points indicated have been determined by using isoelectric focusing, the accuracy of the determination being on the order of ±0,5 pI units.

The properties of the above mannanase preparation differ from those of the known mannanses and it is far more efficient in the hydrolysis of mannopolymers than, for instance, the mannanase isolated from the species *Bacillus subtilis*.

According to the invention the desired enzyme(s) can also be produced by other *Trichoderma reesei* strains, by other strains belonging to the genus Trichoderma and by using other culture media. For this reason the genes coding for the above-metioned enzymes have, in connection with the present invention, been isolated in order to provide the possibility to produce the enzyme by using, for instance, genetically or mutationally improved *Trichoderma reesei* strains or by using other genetically modified production hosts (such as yeast cells) to which the genes coding for the *Trichoderma reesei* mannanases have been transferred.

A novel method for isolating the genes has, at the same time, been developed.

The characteristic features of the invention are indicated in the attached claims.

The term "mannanase" denotes an enzyme which is capable of cleaving polyose chains containing mannose units (mannopolymers). Mannanase therefore covers both endomannanases which internally cleave mannopolymers and exomannanases which cleave mannopolymers from the terminal ends of the chain. As examples of mannopolymers, glucamannan, galactoglucomannan and galactomannan may be mentioned.

Within the scope of the present application, the term "enzyme preparation" designates any product which contains at least one mannanase enzyme. Thus, the enzyme preparation can, for instance, be a culture medium containing a mannanase or several mannanases, an isolated mannanase, or a mixture of two or more mannanases.

By "hybridization" are meant conditions under which different forms of DNA sequences hybridize to DNA sequences coding for a Trichoderma mannanase.

According to the present invention, the mannanase was isolated from the culture medium of *Trichoderma reesei* by using known methods for purifying proteins. For isolating the enzymes anionic and cationic ionexchangers were used as was hydrophobic interaction based chromatography, the isolation of the enzyme being surprisingly easy and fast. The invention is not, however, restricted to this enzyme isolation method, but it is possible to isolate the enzyme with other known methods.

The mannanase activity of the enzyme has been determined by using a method in which an enzyme sample is allowed to act on the mannan of Locust bean for a desired period of time, after which the sugars released are analysed. The method is the following:

A 0.5% solution of Locust bean gum mannan (Sigma G-0753) is prepared in a 50 mM sodium citrate buffer at pH 5.3, and the insoluble solid matter is removed from this mannan solution by centrifugation. To 1.80 ml of the mannan solution 0.200 ml of a suitably diluted enzyme sample is added and it is allowed to act on mannan at +50° C. Exactly 5 minutes after the addition of the enzyme sample 3.00 ml of DNS reagent is added and the mixture formed is heated for 5 min in boiling water. Then, the mixture is cooled with cold water. The colour formed is measured by using spectrophotometer at 540 nm. The amount of reducing sugars in the sample is determined by substracting from the value obtained by spectrophotometer the influence of the reducing sugars contained in the enzyme sample as such, and then comparing the value with values obtained when a mannose solution of known concentration is treated in the same way as the sample. One activity unit (cat/ml) corresponds to the amount of enzyme contained in 1 ml of undiluted sample, which releases 1 mole of reducing sugars per second under the experimental conditions described above.

The invention further describes the specific genes encoding Trichoderma mannanase. Typically, the DNA sequence according to the invention codes for the mannanase of a fungus of the genus Trichoderma and transferred to a yeast or fungal strain induces that strain to produce mannanase.

It should be noted that present knowledge on biochemistry and and molecular biology shows that an enzyme activity suitable for similar application can be provided also by expressing parts of the above-mentioned genes or by expressing gene forms or synthetic genes which differ from the native genes as far as their nucleotide sequences are concerned. Therefore the scope of the invention also covers all forms of genes which remind of the genes described in this invention and which code for a similiar kind of mannanase activity.

Vectors, such as the yeast vectors pMAN1, pMAN2, pMAN3 or pMAN4 described in Example 1, can be formed from the DNA sequence. These vectors inserted into the yeast strain *Saccharomyces cerevisiae* DBY746 have been deposited with the collection Deutsche Sammlung von Mikroorganismen und Zellkulturen GmbH on 30 Dec. 1992 under the numbers DSM 7363, DSM 7364, DSM 7366 and DSM 7365, respectively. The yeast strain used for cloning is described in more detail in the article Penttilä, M. E. et al., Cloning of *Aspergillus niger* genes in yeast. Expression of the gene coding Aspergillus β-glucosidase, Mol. Gen. Genet. 194 (1984), 494–499.

The present invention also provides a method for isolating genes coding for mannanases of, in particular, *Trichoderma reesei*. The method is, however, suited for the isolation of genes coding for mannanases of other microorganisms, as well. The method utilizes an expression library constructed in yeast, in particular in *Saccharomyces cerevisiae*, the genes of the fungus being expressed in the yeast under a yeast promoter. The mannanase protein is extracellularly secreted by the yeast and the yeast clones containing the mannanase gene can be found on basis of their production of mannanase activity, which can be detected by enzyme activity tests or by plate assays. Alternatively, the yeast producing mannanase activity can be found, for instance, by using the antibody corresponding to the mannanase. The enzyme activity based method is a particularly preferred alternative for isolating mannanase genese because it makes it possible to find the yeasts producing the active mannanase enzyme and the genes can be isolated from these yeasts for characterization. The yeast expression library can be constructed using some other yeast promoter, even a promoter providing a lower expression level. It is possible also to use the mannanase gene's own promoter, and the genes can be isolated by using a chromosomal gene library. The gene library can be constructed also, for instance, in a single-copy plasmid.

Based on the above, the method according to the invention for isolating genes coding for mannanases can be defined by the following preferred method steps:

The messenger RNA pool of a microorganism producing mannanase activity is enriched in respect of the messenger RNA of the mannanase by culturing the microorganism in conditions which will induce the mannanase production of said microorganism. The mannanase production is induced by, e.g., mannan-containing and/or cellulose-containing culture media. Messenger RNA is isolated from the microorganism and the cDNA corresponding to the isolated mRNA is prepared. Then the cDNA thus obtained is placed in a vector under the control of a yeast promoter and the recombinant plasmids obtained are transformed into a yeast strain, which naturally does not produce the corresponding mannanase, in order to provide an expression library. The yeast clones thus obtained are then cultured on a culture medium in order to express the expression library in the yeast. The yeast clones producing the mannanase are separated from the other yeast clones, and the plasmid-DNAs of said separated yeast clones are isolated. If desired, the DNA is sequenced in order to determine the DNA sequence coding for the mannanase.

As mentioned above, the mannanase-producing microorganism used in the method preferably comprises a fungus and in particular a fungal strain belonging to the genus Trichoderma. According to one preferred embodiment the fungus is cultivated on a culture medium comprising at least mannan- (e.g. galactomannan) and/or cellulose-containing substrate as carbon source and in addition possibly acetyl glucurono xylan and/or xylan. As Example 2 below will show, the culture medium can for instance contain a combination of all these substances and as nitrogen source, for instance, corn steep syrup.

In the following step of the method the recombinant plasmids are preferably transferred to a yeast strain belonging to the genus Saccharomyces, in particular to the strain *Saccharomyces cerevisiae*, which is cultivated for producing mannanase. The yeast promoter of the plasmid vector can be, for instance, PGK or a similar promoter which is considered to be strong. The yeast clones can be cultivated on different substrates such as glucose and galactose. The culture medium is selected depending on under which promoter the gene is placed. According to the invention, it is also possible to use a yeast vector, wherein the promoter can be induced by galactose, the hydrolase genes being expressed by galactose and not by, for instance, glucose. The benefit of the promoter PGK is a strong level of expression which is advantageous as far as enzymes having a low catalytic activity are concerned. It is also easy to manipulate it. As described in more detail in Example 1, the plasmid vector used, can comprise, for instance, vector pAJ401, which is prepared from vector pFL60 by cutting it with restriction enzymes and ligating to it an adapter consisting of oligonucleotides. The cDNA synthetized from the messenger RNA is then ligated between the promoter and terminator of vector pAJ401, downstream from the promoter.

It should be noticed that, within the scope of the present invention, the mannanase genes can, in principle, be isolated by all other commonly known methods, for instance by constructing an expression library into an *E. coli* strain bacterium, e.g. into a lambda vector, whereby the clone containing the gene corresponding to a certain protein can be found by, e.g. the antibody corresponding to the protein. The gene can also be found by using oligonucleotides corresponding to the N-terminal amino acid sequence of the mannanase protein as a probe in gene library hybridization.

The present invention relates to the expression of mannanase genes of the fungus *T. reesei* in yeast and to the secretion of the active gene product into the culture medium of the yeast. Because *S. cerevisiae* normally does not produce mannanase activity, a recombinant yeast which produces *T. reesei* mannase can be used as such for producing an enzyme composition containing a specific mannanase. The prior art is completely silent about the expression of mannanase genes in foreign host organisms. Our invention shows that fungal mannanase can be produced in yeast, which means that the invention includes the production of mannanase enzyme in other yeast strains as well, for instance in yeast strains belonging to the genera Kluyveromyces, Pichia and Hansenula. The mannanase gene can be transferred to other fungi, such as strains of the genera Aspergillus, Penicillium, Neurospora and Phanerochaete, by methods known per se and the fungus can be made to secrete active Trichoderma mannanase. Even the mannanase production of Trichoderma itself can be improved or modified after gene isolation by known gene technical means, by, for instance, transferring several copies of the chromosomal mannanase gene into the fungus or by placing the gene under the (e.g. stronger) promoter of another gene and thus to provide mannanase expression under desired growth conditions, such as on culture media which natively do not produce mannanases. The invention covers the organisms producing said Trichoderma mannanases.

The recombinant yeast or fungal strain according to the invention is therefore characterized in that it contains a DNA sequence which codes for a mannanase of a fungus of the genus Trichoderma. The yeast strain is preferably a strain of the species *Saccharomyces cerevisiae*, such as S.c.man1, S.c.man2, S.c.man3 or S.c.man4 (cf. Example 1 below). The recombinant fungal strain is preferably a strain belonging to the genus Trichoderma.

Based on the above, the invention also provides a method for constructing yeast strains which are capable of expressing mannanase. According to the method DNA sequences coding for mannanase are isolated from a suitable fungus species, a yeast vector is formed from the DNA sequence and the yeast vector is transferred to a suitable yeast strain. For instance, the yeast vectors are transferred to a yeast strain selected from the group comprising strains of genera Saccharomyces, Kluyveromyces, Pichia or Hansenula.

The invention also comprises a method for producing mannanase enzyme, which method comprises isolating the DNA sequence coding for mannanase from a fungus of the strain *Trichoderma reesei*, forming a vector containing said DNA sequence, which is then transferred to a suitable yeast or fungus strain for achieving a recombinant strain. Said recombinant strain is then cultivated under conditions which enable the strain to express mannanase. The mannanse produced is recovered, for instance, by isolating it from the culture medium.

The mannanase preparations produced according to the invention can be advantageously used for hydrolysis of mannopolymers, in particular in connection with cellulosic pulp bleaching. The mannanses used in bleaching comprise mannanases isolated from *T. reesei* (or produced in any of the above-mentioned ways) either in the form of a mixture, in purified form or in culture medium. The mannanases can be used together with xylanase. According to a particularly preferred embodiment a combined mannanase/xylanase treatment is carried out in connection with bleaching employing chlorine chemicals. Chlorine free bleaching processes (e.g. peroxide bleaching) provide rather good results already by a mannanase enzyme preparation. The enzyme treatment makes it possible even further to increase the extraction of residual lignin in chemical bleaching, and the method is therefore as well environmentally as economically advantageous.

By means of the mannanase treatment described in this invention it is possible to achieve an increase of the brightness produced by, in particular, totally chlorine free pulp bleaching sequences, which cannot be obtained with peroxide only or with any other chemical at so low costs or without impairing the strength of the pulp. The mannanase treatment according to the invention combined with a xylanase treatment improves brightness particularly when it is used in connection with both conventional chlorine-based bleaching sequences and totally chlorine chemical free bleaching sequences. In conventional chlorine bleaching, the pulp can be bleached with a standard dosage of the chemical to a higher final brightness or, alternatively, by adding enzymes it is possible to lower the chemical dosage in the initial stage of the bleaching when a certain brightness level is aimed at, which makes it possible to reduce the detrimental impact on the environment.

The higher efficiency of the enzymes make it possible directly to affect the type and amount of the chemicals used for industrially extracting lignin from the fibres and, thus, to improve the low-chlorine or chlorine-free bleaching methods which are environmentally advantageous.

The invention is described in more detail with the help of the following non-limiting examples.

In the Examples reference is made to the attached drawings, whereby.

EXAMPLE 1

Isolation of mannanase genes and expression in yeast

*Trichoderma reesei*-strain QM 9414 was cultivated in a fermentor for 42 h on a cultivation medium containing (per litre): 20 g of Solca floc cellulose, 10 g of Locust bean gum galactomannan (Sigma), 5 g of $KH_2PO_4$, and 5 g of $(NH_4)_2SO_4$. After the 42 hours of growth, 1 g of lactose, 1 g of Birke 150 acetylglucuronoxylan and 1 g of Oat Spelt xylan was added for each litre of cultivation medium, and the fungus was cultivated for further 24 h. The RNA was isolated from the fungus as described by Chirgwin et al. (1979), and the poly A+mRNA was isolated by chromatography through oligo(dT) essentially as described (Maniatis et al., 1982). cDNA was synthesized by using the ZAP-cDNA synthesis kit from Stratagene and it was ligated to the plasmid vector pAJ401. Plasmid pAJ401 was derived from plasmid pFL60 (Minet & Lacroute, 1990) by cutting it with EcoRI and XhoI restriction enzymes and by ligating inbetween an adapter, which was obtained by combining the oligonukleotides 5'-tcgaagaattcgagagactcgagt-3' and 3'-tcttaagctctctgagctcattaa-5'. The orientation of the restriction sites of enzymes EcoRI and XhoI was then reversed in the plasmid. The synthetized cDNA was ligated to the pAJ401 vector cut with EcoRI and XhoI between the PGK promoter and terminator. The 5' end of the cDNA is bound downstream from the PGK promoter during cloning. The ligating mixture was transformed into the *E. coli* strain PLK-F' by electroporation (Dower et al., 1988).

Figure 1:
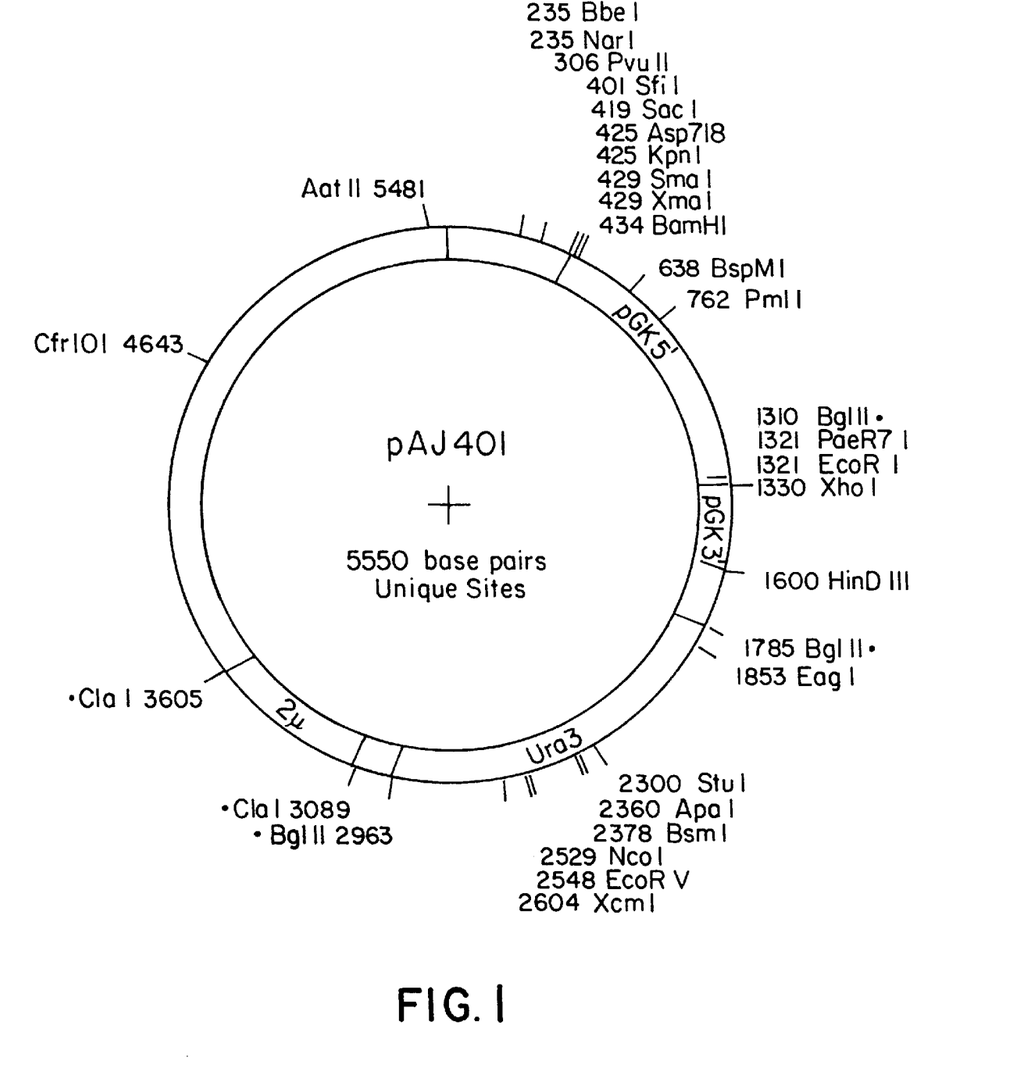
FIG. 1 shows the structure of plasmid pAJ401 constructed from plasmid pFL60.
Figure 2:
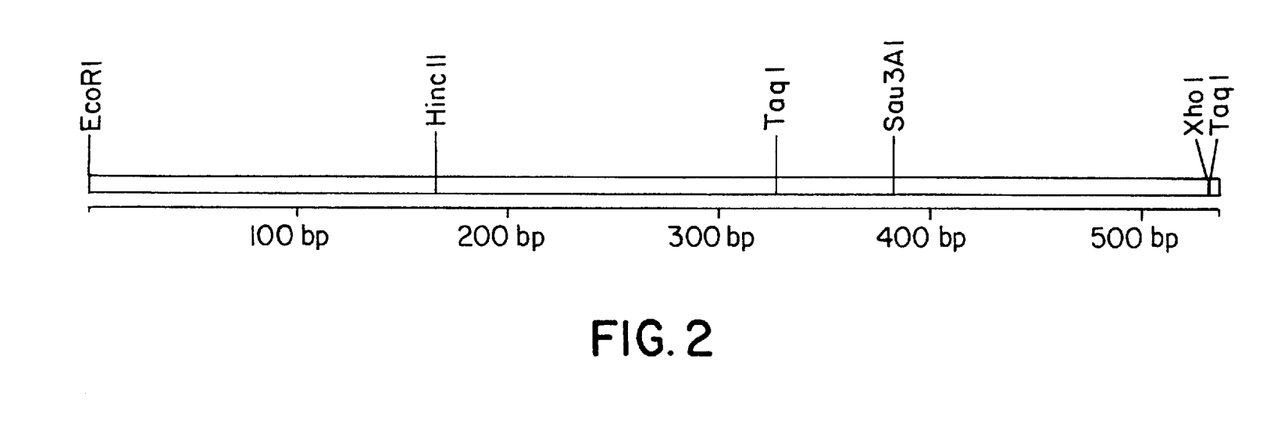
FIG. 2 shows the restriction sites of the mannanase-coding insert of yeast vector pMAN1.
Figure 3:
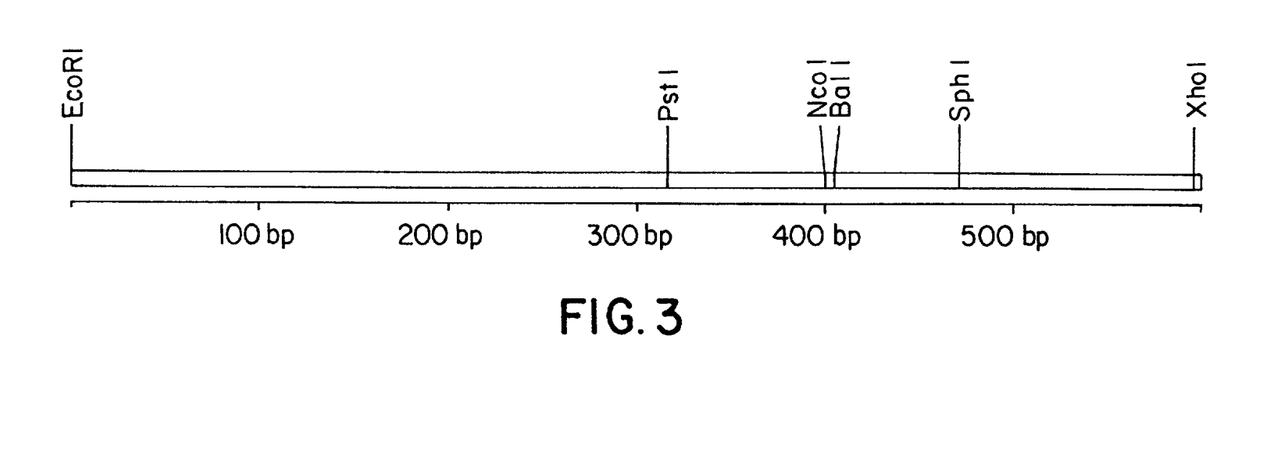
FIG. 3 shows the restriction sites of the mannanase-coding insert of yeast vector pMan2.
Figure 4:
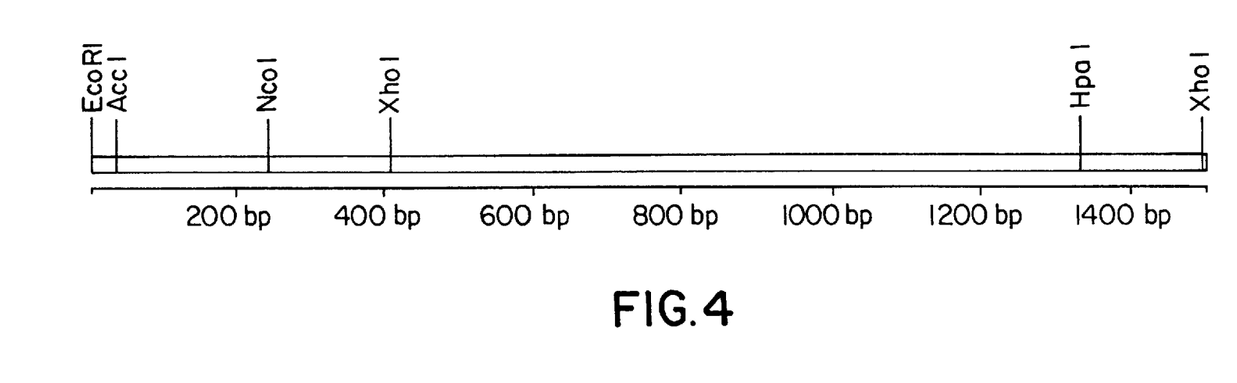
FIG. 4 shows the restriction sites of the mannanase-coding insert of yeast vector pMAN3.
Figure 5:
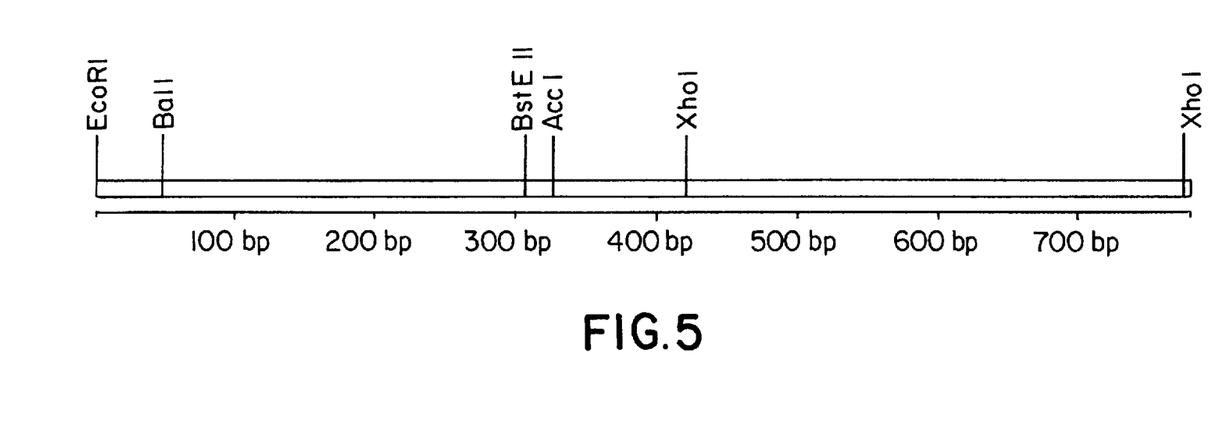
FIG. 5 shows the restriction sites of the mannanase-coding insert of yeast vector pMAN4.

The structure of plasmid pAJ401 is shown in the figure.

The gene library plasmids were isolated as one batch from about 42,000 bacterial colonies and transformed into the *Saccharomyces cerevisiae* yeast strain DBY746 (Penttilä et al., 1984) by electroporation (Becker & Guarante 1990) while selecting the transformants on a Sc medium which is deficient in uracil. The yeast colonies were scraped from the plates and maintained as one batch in a Sc-ura-medium containing 15% glycerol at −70° C.

For isolating the mannanase genes the gene library mixture was pipeted onto substrate-containing plates (yeast minimal medium plates, containing for each 1000 ml: 0.058 g histidine, 0.082 g tryptophan, 0.262 g leucine and 0.1% Locust bean gum (0.5% stock solution in 50 mM citrate buffer at pH 5.3. In all about 100,000 gene library clones were tested for mannanase activity after one week of cultivation by replicating first the colonies from the plates, then flushing the plates with water, and by staining the plates with a 0.1% solution of Congo Red. Yeast colonies producing hydrolysis halos were picked up from the replica plates and they were tested again for mannanase activity on plate assay.

Four mannanase-positive yeast clones were called *Saccharomyces cerevisiae* man1, S.c. man2, S.c. man3 and S.c. man4. These strains were deposited into the collection Deutsche Sammlung von Mikroorganismen und Zellkulturen GmbH on the 30th of Dec. 1992 under the numbers DSM 7363, DSM 7364, DSM 7366 and DSM 7365, respectively.

The yeast clone S.c. man1 (DSM 7363) contains the yeast vector pMAN1, which consists of the plasmid pAJ401, having a 0.7 kb mannanase coding insert in the restriction sites of restriction enzymes EcoRI and XhoI.

The yeast clone S.c. man2 (DSM 7364) contains the yeast vector pMAN2, which consists of the plasmid pAJ401, having a 0.7 kb mannanase coding insert in the restriction sites of restriction enzymes EcoRI and XhoI.

The yeast clone S.c. man3 (DSM 7366) contains the yeast vector pMAN3, which consists of the plasmid pAJ401, having a 1.4 kb mannanase coding insert in the restriction sites of restriction enzymes EcoRI and XhoI.

The yeast clone S.c. man4 (DSM 7365) contains the yeast vector pMAN2, which consists of the plasmid pAJ401, having a 1.0 kb mannanase coding insert in the restriction sites of restriction enzymes EcoRI and XhoI.

The DNA of the mannanase positive yeast clones was isolated (Sherman et al 1981), and used for transformation of the *E. coli* strain DH5α. From the ampicillin-positive transformants plasmid DNA was isolated by conventional methods and digested by several restriction enzymes, to determine which clones contained the same mannanase gene. The clones were sequenced by conventional methods to obtain a suitably long a clone from each gene.

The cDNA sequence of the mannanase genes was determined by conventional methods. The nucleotide sequence of the insert of the vector pMAN1 is indicated in sequence list SEQ NO. 1.

The chromosomal copies were also isolated from the clones using the previously prepared gene library (Vanhanen et al. 1989), and the 5' end of the gene was sequenced by utilizing primers specific for the 5' end designed on basis of the cDNA sequence. Sequence listing SEQ ID NO. 2 shows the nucleotide sequence of the 5' end and sequence listing SEQ ID NO. 3 the nucleotide sequence of its 3' end. Sequence listing SEQ ID NO. 4 indicates the 5' end of the insert of vector pMAN3 and sequence listing SEQ ID NO. 5 the 3' end thereof.

EXAMPLE 2

Isolation of mannanase genes

This example illustrates an alternative way of isolating mannanase genes from a gene library mixture. *Trichoderma reesei* strain QM 9414 was cultivated, the gene library plasmids were formed and the genes were expressed in yeast as described in Example 1.

The gene library mixture was pipated into the Sc-ura cultivation medium on microtiter plates so that each well of the microtiter plates contains an avarage of 70 different yeast library clones, in total about 75,000 clones. The microtiter plates were cultivated for 4 days and the cells were centrifuged to the bottom of the wells. The supernatants were tested for their mannanase activity by using Locust bean gum as a substrate. (cd. above). Some of the wells contained mannanase activity, and the yeast cells contained in said wells were plated onto Sc-ura-plates as separate colonies. About 130 separate colonies of each well were retested for their mannanase activity in order to identify single yeast clones containing the mannanase gene.

EXAMPLE 3
Cultivation and characterization of the yeast clones

This example describes an alternative embodiment for characterization of yeast clones containing mannanase genes.

Yeast clones S.c.man1, S.c.man2, S.c.man3 and S.c.man4, which correspond to plasmid clones pMAN1, pMAN2, pMAN3 and pMAN4, were obtained by following the procedure described in Example 1. The clones were cultivated on a Sc-ura cultivation medium for 2 days in a flask and the supernatant was analysed by the Western blot-method using antibodies prepared against purified mannanases obtained from *T.reesei*. The 5' end of the nucleotide sequence obtained from the clones was also compared with the N-terminal sequence from the purified mannanases. It was thus ascertained which isolated mannanase genes correspond to the earlier purified mannanase proteins.

EXAMPLE 4
Isolation of the enzyme

In order to isolate the enzyme, the culture medium of *Trichoderma reesei* (Rut C-30, VTT D-86271) was first treated with bentonite, as described by Zurbriggen et al. (1990). Then the solution was concentrated by ultrafiltration and the concentrate was dried by spray drying.

The isolation of the enzyme was started by dissolving the spray dried culture medium in a phosphate buffer. The insoluble material was separated by centrifugation and the enzyme solution was buffered by gel filtration to pH 7.2 (Sephadex G-25). The enzyme solution was pumped at this pH through a cation exchange chromatography column (CM-Sepharose FF), to which a part of the proteins of the sample were bound. The desired enzyme was collected in the fractions eluted through the column.

At said pH (pH 7.2) the enzyme solution was pumped to an anion exchange chromatography column (DEAE-Sepharose FF), to which most of the proteins of the sample were bound. The desired enzyme was collected in the fraction eluted through the column.

The enzyme-containing fractions were further purified by using hydrofobic interaction chromatography (Phenyl Sepharose FF). The enzyme was bound to said material at a salt concentration of 0.3M $(NH_4)_2SO_4$. The bound enzyme was eluted with a buffer at pH 6.5, so as to form a decreasing linear concentration gradient of $(NH_4)_2SO_4$ from 0.3 to 0M. After this, elution was continued with the buffer of pH 6.5. The mannanase enzyme was collected at the end of the gradient and in the fractions collected after that.

The enzyme solution was buffered by gel filtration to pH 4.3 (Sephadex G-25). The enzyme was bound at this pH to a cation exchange chromatography column (CM-Sepharose FF), and a part of the proteins bound to the column (i.a. most of the remaining cellulases) were eluted with a buffer, pH 4.4. The mannanase enzyme was eluted with a buffer, pH 4,3, to which sodium chloride was added in order to form a linear concentration gradient of sodium chloride from 0 to 0.05M. The purified enzyme was collected in the fractions eluted by the gradient.

EXAMPLE 5
Enzyme characterization

The protein properties of the enzyme preparation purified according to Example 1 were determined by methods known per se in protein chemistry. The molecular weights were determined by the SDS-PAGE-method, the accuracy of which is about ±10%

The preparation contains two mannanase isoenzymes, which biochemically and functionally proved to be almost identical. The isoenzymes are named EM 3 and EM 4. Their properties are described in Table 1.

TABLE 1

Properties of the *Trichoderma reesei* mannanase

| Property | Unit | EM 3 | EM 4 |
| --- | --- | --- | --- |
| Molecular weight under denaturating conditions | kDa | 51 | 53 |
| Isoelectric point |  | 4.5 | 5.4 |
| Relative specific activity | percentage of the activity of the reference substance |  |  |
| reference[a] |  | 100 | 100 |
| guar mannan |  | 45 | 40 |
| Insoluable mannan of Corozo nut |  | 7 | 9 |
| Soluable mannan of the Corozo nut |  | 126 | 145 |
| Optimum pH |  | 3–5.3 | 3–5.3 |
| Optimum temperature at for activity testing | °C. | 70 | 70 |
| Hydorlysation products of β-1,4-mannan |  | $M_2, M_3$ | $M_2, M_3$ |

[a]: Locust bean gum
$M_2$: mannobiose
$M_3$: mannotriose

The N-terminal amino acid sequences of enzymes EM3 and EM4 have also been determined and they are indicated in sequence listings SEQ ID NO. 6 and SEQ ID NO. 7. respectively.

EXAMPLE 6
Mannanases secreted by *Trichoderma reesei* into its culture medium The fungus *Trichoderma reesei* (VTT-D-86271) was cultivated in a fermentor for 5 days on a culture medium, whose main components were cellulose and corn steep syrup. After the cultivation the cells were separated from the solution by centrifugation and the mannanase activity of the culture medium was characterized by isoelectric focusing, ionexchange chromatography and chromatofocusing.

The isoelectric focusing was made by Phast equipment (Pharmacia-LKB) according to the instructions by the manufacturer on a gel supplied by the same manufacturer. A pH gradient from pH 3 to pH 9 was formed in the gel during focusing. After the isoelectric focusing time the proteins were transferred from this gel to a staining gel which contained Locust bean gum mannan. By staining with Congo red, the location of the mannanase proteins could be detected on this gel, which made it possible to estimate the isoelectric point of the mannanase enzymes.

Each isoenzyme's relative portion of the total mannanase activity isoenzyme was estimated by running chromatofocusing on a PBE 94 gel supplied by Pharmacia-LKB according to the instructions of the manufacturer. The mannanase activity of the fractions obtained was measured and they were then subjected to an activity staining as described above. Furthermore the different fractions of the purification procedure were, if needed, subjected to activity staining in addition to mannanase determination. These methods made it possible to make an estimation of the relative amounts of the enzymes in the solution of the Example with an accuracy of 10 to 20%.

Table 2 indicates the isoelectric points of the mannanase enzymes and their relative activities.

TABLE 2

Isoelectric points of the *Trichoderma reesei* mannanases and their relative portions of the total mannanase activity

|     | pI  | Estimated portion of the mannanase activity (%) |
| --- | --- | --- |
| EM1 | 3.8 | 5–15 |
| EM2 | 4.1 | 10–30 |
| EM3 | 4.5 | 30–40 |
| EM4 | 5.4 | 30–40 |
| EM5 | 6.5 | <5 |

EXAMPLE 7
Hydrolysis of cellulosic pulp

Pine kraft pulp, pine saw dust and glucomannan fractions isolated from them were hydrolysated with *T. reesei* mannanase. The enzyme dosage was 5000 nkat/g calculated on basis of the glucomannan. The treatment was carried out in 50 mM citrate buffer at pH 5.0. The treatment lasted for 24 h and the temperature was 45° C. After the treatment the dissolved sugars were determined after acid hydrolysis. The result is indicated in percent of the original glucomannan which was hydrolyzed. (Table 3).

TABLE 3

The relative amounts of hydrolyzed glucomannans

| Substrate | percentage of hydrolyzed glucomannan |
| --- | --- |
| pine saw dust | 11 |
| mannan isolated from pine tree | 65 |
| pine kraft pulp | 10 |
| mannan isolated from pine kraft pulp | 79 |

Thus, the mannanase are efficient in hydrolyzing mannan isolated from both pine tree and pine kraft pulp. As a result of the hydrolysis, glucomanno-oligomers are formed.

EXAMPLE 8
Bleaching of cellulose pulp (mannanase pretreatment)

Pine kraft pulp (kappa 26.2) was treated with *T. reesei* mannanase at 5% consistency for 2 h at pH 5 and 45° C. After the treatment the pulp was washed (2×10×dry matter of the pulp) and bleached with a 1-stage peroxide sequence. Subsequent to the peroxide stage the pulp was acidified and its brightness, kappa and viscosity were determined. The results are indicated in Table 4. The chemical dosages and conditions were: $H_2O_2$ 3%, NaOH 1.5%, DTPA 0.2%, $MgSO_4$ 0.5%, 80° C., 1 h.

TABLE 4

Peroxide bleaching of kraft pulp subsequent to mannanase treatment

| Dose nkat/g | Released reducing sugars in % of dry matter | Kappa | Brightness, % | Viscosity dm³/kg |
| --- | --- | --- | --- | --- |
| 100 | 0.25 | 13.9 | 42.9 | 970 |
| 500 | 0.48 | 13.5 | 43.2 | 940 |
| ref | 0 | 17.6 | 41.0 | 980 |

After a simple mannanase treatment, the kappa reduction during the peroxide stage was 23% better than in the reference test.

EXAMPLE 9
Bleaching of cellulose pulp

The procedure described in Example 5 was followed with the difference that coniferous pulp was treated with mannanase and xylanase. The pulp was subjected to peroxide bleaching similiar to the one of Example 4. The results appear from Table 5.

TABLE 5

Bleaching with peroxide of kraft pulp after mannanase/xylanase treatment

| Enz. | Dose nkat/g | Reducing sugars in % of dry matter | Kappa | Brightness, % | Viscosity dm³/kg |
| --- | --- | --- | --- | --- | --- |
| XYL + MAN | 100 + 100 | 0.45 | 12.8 | 45.0 | 990 |
| XYL + MAN | 100 + 500 | 0.9 | 11.8 | 44.8 | 950 |
| XYL | 100 | 0.41 | 16.8 | 43.7 | 990 |
| ref | — | 0 | 17.6 | 41.0 | 980 |

XYL = xylanase
MAN = mannanase

Combination of the mannanase treatement with a xylanase treatment lowered the kappa of the peroxide bleached pulp by 32% compared to the reference treatment.

EXAMPLE 10
Bleaching test carried out for cellulose pulp

Pine kraft pulp cooked in a laboratory (kappa 34.4) was treated with mannanase purified from *T. reesei* at a consistency of 5%, at pH 5 and at a temperature of 45° C. After the treatment the pulp was washed and bleached with the sequence (D50/C50)EDED.

TABLE 6

Bleaching with chlorine chemicals of coniferous pulp treated with enzymes

| Enz. | Dose nkat/g | Chlorination factor | Int. kappa | Brightness, % | Viscosity dm³/kg |
| --- | --- | --- | --- | --- | --- |
| MAN | 90 | 0.15 | 6.4 | 88.4 | 1050 |
| XYL pI9 | 100 | 0.15 | 5.6 | 89.5 | 1080 |
| MAN + XYL | 90 + 100 | 0.15 | 5.2 | 90.3 | 1060 |
| ref | — | 0.15 | 6.5 | 88.1 | 1050 |
| ref | — | 0.18 | 4.5 | 90.5 | 1050 |

In comparison to a simple xylanase treatment, a combined xylanase and mannanase treatment provided a considerably much smaller intermittent kappa and a higher final brightness.

EXAMPLE 11
Bleaching of mannanase-treated sulphite pulp

Coniferous sulphite pulp was treated with mannanase at 5% consistency at pH 5 and a temperature of 45° C. for 2 h. After the treatment the pulp was washed and bleached with a one-stage peroxide sequence. After the peroxide stage the brightness, kappa and viscosity of the pulp were determined. The chemical dosages were: 1.5% $H_2O_2$, 1.2% NaOH 1,2% and 0.05% $MgSO_4$. The bleaching time was 60 min at 80° C. (Enz=XYL 100, XYL 100+500, MAN 500).

It was found that the mannanase treatment made it possible to improve the bleachability of sulphite pulp.

EXAMPLE 12
Bleaching test of kraft pulp treated with mannanase and xylanase

Coniferous kraft pulp (spruce/pine) was treated with mannnase and xylanase as in Example 7. After the treatment the pulp was washed and bleached by the sequence D(ED) DED. The bleaching conditions are shown in Table 7A.

After the mannanase treatment the intermittent kappa and the brightness were better than in the reference pulp. When the mannanase treatment was combined with a xylanase treatment the intermediate kappa was much lower and an over 90% final brigthness was obtained with a 15% saving in chemical consumption (Table 7B).

TABLE 7A

Bleaching conditions.
Bleaching sequence: D(EP)DED). Chlorination factors 0.15 and 0.20.

| Stage | Consistency % | T °C. | Duration min. | Final pH | Act. Cl % | P % | NaOH % |
|---|---|---|---|---|---|---|---|
| D0 | 3 | 60 | 60 | 2.0–1.9 | $3.3^{1,3}$ $4.3^{2)}$ | | |
| EP | 10 | 80 | 60 | 10.4–10.5 | | 0.3 | $1.7^{1,3}$ $2.1^{2)}$ |
| D1 | 10 | 70 | 180 | 3.4–3.6 | $2.5^{1,2)}$ $3.0^{3)}$ | | |
| E2 | 10 | 70 | 60 | 10.8–10.9 | | | 0.9 |
| D2 | 10 | 70 | 180 | 3.8–4.1 | $0.5 . 1.0^{1,3}$ 0.7 | | |

[1] Enzyme treated pulp, chlorination factor 0.15
[2] Chlorination factor 0.20
[3] Reference, chlorination factor 0.15

TABLE 7B

Chlorine bleaching of mannanase and xylanase treated pulps. Sequence D(EP)DED. Initial kappa of pulp: 21.6.

| Enzyme | Dosage, nkat/g | Reducing sugars, % of dry matter | Chlorination factor | Intermediate kappa | D-1 brightness % | Final brightness % | Viscosity dm³/kg | Chemicals consumption % act. Cl |
|---|---|---|---|---|---|---|---|---|
| MAN | 500 | 0.40 | 0.15 | 6.2 | 80.1 | 89.8 | 940 | 6.7 |
| XYL | 100 | 0.38 | 0.15 | 5.5 | 82.5 | 90.2 | 980 | 6.4 |
| MAN + XYL | 500 + 100 | 0.70 | 0.15 | 5.2 | 83.5 | 90.7 | 960 | 6.3 |
| ref | — | — | 0.15 | 6.5 | 79.8 | 89.7 | 970 | 7.1 |
| ref | — | — | 0.20 | 5.1 | 82.8 | 90.1 | 970 | 7.4 |

References

Becker, D. M. & Guarante, L. (1990) High efficiency transformation of yeast by electroporation. Meth. Enzymol. 194:182–.

Beldman, G., Searle-van Leeuwen, M. F., Rombouts, F. M. and Voragen, F. G. J. (1985) The cellulase of Trichoderma viride Purification, characterization and comparision of all detectable endoglucanases, exoglucanase and β-glucosidases. Eur. J. Biochem. 146:301–308.

Bisaria, V. S. and Ghose, T. K. (1981) Biodegradation of cellulosic materials: substrates, micro-organisms, enzymes and products. Enzyme Microb. Technol. 3:90–104.

Chirgwin, J. M., Przybyla, A. E., MacDonald, R. J., and Rutter, W. J. (1979) Isolation of biologically active ribonucleic acid from sources enriched in ribonuclease. Biochemistry 18:5294–5299.

Clark T. A., McDonald A. G., Senior D. J., Mayers P. R. (1990), Abstr. 4th Int. Conf. on Biotechnology in the Pulp and Paper Industry, Raleigh 1989, pp. 39–40.

Clark, T. A., Steward, D., Bruce, M. E., McDonald, A. G., Singh, A. P. and Senior, D. J. (1991) Proc. 45th APPITA Annual General Conference, Melbourne 1991, Vol. I, pp. 193–200.

Dower, W. J., Miller, J. F. & Ragsdale, C. W. (1988) High efficiency transformation of E. coli by high voltage electroporation. Nucl. Acids Res. 16:6127–6145.

Kantelinen, A., Rättö, M., Sundquist, J., Ranua, M., Viikari, L. and Linko, M. (1988) Hemicellulases and their potential role in bleaching. 1988 International Pulp Bleaching Conference. Tappi Proceedings, 1–9.

Kantelinen, A., Sundquist, J., Linko, M. and Viikari, L. (1991) The role of reprecipitated xylan in the enzymatic bleaching of kraft pulp. Proc. 6th International Symposium on Wood and Pulping Chemistry, Melbourne 1991, Vol. I, pp. 493–500.

Luce, J. E. (1964) Radial distribution of properties through the cell wall. Pulp and Paper Magazine of Canada 65, 419–423.

Lyr, H. (1963) Occurence of mannanases in fungi. Z. Allgem. Mikrobiol. 3, 25–35.

Maniatis, T., Fritsch, E. F. and Sambrook, J. (1982) Molecular cloning. A laboratory manual. Cold Spring Harbor Laboratory, New York.

Minet & Lacroute (1990) Curr. Genet. 18:287–291.

Penttilä, M. E., Nevalainen, K. M. H., Raynal, A. & Knowles, J. K. C. (1984) Cloning of Aspergillus niger genes in yeast. Expression of the gene coding Aspergillus β-glucosidase. Mol. Gen. Genet. 194:494–499.

Poutanen, K. Rättö, M., Puls, J. and Viikari, L. (1987) Evaluation of different microbial xylanolytic systems. J. Biotechnol. 6:49–60.

Reese, E. T. and Shibata, Y. (1965) β-Mannanases of fungi. Can. J. Microbiol. 11: 167–183.

Sherman, F., Fink, G. R. and Hicks, J. B. (1981) Methods in Yeast Genetics. Cold Spring Harbor Laboratory, New York.

Simonson, R. (1971) The hemicellulose in the sulfate pulping process. Svensk Papperstidning 74, 691–700.

Sjöström, E. (1977) The behavior of wood polysaccharides during alkaline pulping processes. Tappi 60, 151–154.

Timell, T. E. (1967) Recent progress in the chemistry of wood hemicelluloses. Wood Science and Technology 1, 45–70.

Vanhanen, S., Penttilä, M., Lehtovaara, P. & Knowles, J. (1989) Isolation and characterization of the 3-phosphoglycerate kinase gene (pgk) from the filamentous fungus Trichoderma reesei. Curr. Genet. 15:181–186.

Viikari, L., Ranua, M., Kantelinen, A., Linko, M. and Sundquist, J. (1986) Bleaching with enzymes. Biotechnology in the Pulp and Paper Industry, Proc. 3rd Int. Conf., Stockholm, pp. 67–69.

Viikari, L., Ranua, M., Kantelinen, A., Linko, M. and Sundquist, J. (1987) Application of enzymes in bleaching. Proc. 4th Int. Symp. Wood and Pulping Chemistry, Paris, Vol. 1, pp. 151–154.

Viikari, L., Kantelinen, A., Poutanen, K. and Ranua, M. (1990) Characterization of pulps treated with hemicellulolytic enzymes prior to bleaching. In: Kirk, K. T. and Chang, H.-M. (eds), Biotechnology in Pulp and Paper Manufacture, Butterworth-Heinemann, Boston, pp. 145–151.

Viikari, L., Kantelinen, A., Rättö, M. and Sundquist, J. (1991a) Enzymes in pulp and paper processing. In: Leatham, G. F. and Himmel, M. E. (eds), Enzymes in Biomass Conversion, ACS Symp. Ser. 460, American Chemical Society, Washington, D.C., pp. 12–22.

Viikari, L., Sundquist, J. and Kettunen, J. (1991b) Xylanase enzymes promote pulp bleaching. Paper and Timber 73, 384–389.

Yllner, S. and Enström, B. (1956) Studies of the adsorption of xylan on cellulose fibres during the sulphate cook. Part 1. Svensk Papperstidning 59, 229–232.

Yllner, S., Östberg, K. and Stockman, L. (1957) A study of the removal of the constituents of pine wood in the sulphate process using a continuous liquor flow method. Svensk Papperstidning 60, 795–802.

Zurbriggen, B., Bailey, M., Penttilä, M., Poutanen, K. and Linko, M. (1990). J. Biotechnol. 13:267–278.

Zurbriggen, B. D., Penttilä, M. E., Viikari, L. & Bailey, M. J. (1991). Pilot scale production of fungal endo-β-glucanase by brewer's yeast. J. Biotechnol. 17:133–146.

We claim:

1. A culture medium comprising an elevated level of one or more mannanase enzymes endogenous to *T. reesei* and produced by one or more microorganisms, wherein said one or more mannanase enzymes is present at a level which is higher than the level produced under the same growth conditions by a wild-type form of the microorganism which produced the mannanase.

2. A culture medium of claim 1, wherein said culture medium is of a fungus.

3. The culture medium of claim 2, wherein said fungus is selected from the group consisting of Aspergillus, Penicillium, Neuospora, Phanerochaete and Trichoderma.

4. The culture medium of claim 3 wherein said fungus is Trichoderma.

5. The culture medium of claim 1 or claim 2 wherein one or more microorganisms which produce said one or more mannanase enzymes have been removed.

6. The culture medium of claim 1 or claim 2 wherein about 30–40% of the mannanase activity comes from a mannanase having a pI of about 4.5 and about 30–40% of the mannanase activity in said medium comes from a mannanase having a pI of about 5.4 and the remaining 20–40% of mannanase activity is from one or more additional mannanase enzymes endogenous to *T. reesei*.

7. A culture medium comprising elevated levels of EM3 mannanase and EM4 mannanase.

8. A cell free culture medium comprising an elevated level of one or more mannanase enzymes endogenous to *T.reesei* and produced by one or more microorganisms, wherein said one or more mannanase enzymes is present at a level which is higher than the level produced under the same growth conditions by a wild-type form of the microorganism which produced the mannanase.

9. The culture medium of claim 1 wherein the concentration of said one or more mannanase enzymes is higher than the concentration of said one or more mannanase enzymes found in a culture medium of wild-type *T. reesei*.

* * * * *